United States Patent
Yi et al.

(10) Patent No.: US 11,179,410 B2
(45) Date of Patent: Nov. 23, 2021

(54) PHARMACEUTICAL COMPOSITION FOR IMPROVING, PREVENTING OR TREATING MUSCLE RELATED DISEASE COMPRISING GINSENOSIDE RH2

(71) Applicant: KOREA ADVANCED INSTITUTE OF SCIENCE AND TECHNOLOGY, Daejeon (KR)

(72) Inventors: Gwan-Su Yi, Daejeon (KR); Yi Li, Daejeon (KR); Yoon Hyeok Lee, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 88 days.

(21) Appl. No.: 16/406,156

(22) Filed: May 8, 2019

(65) Prior Publication Data
US 2019/0343855 A1    Nov. 14, 2019

(30) Foreign Application Priority Data
May 10, 2018 (KR) .................. 10-2018-0053669

(51) Int. Cl.
```
A61K 36/258    (2006.01)
A61K 31/704    (2006.01)
A23L 33/105    (2016.01)
A61P 21/00     (2006.01)
```

(52) U.S. Cl.
CPC .......... *A61K 31/704* (2013.01); *A23L 33/105* (2016.08); *A61K 36/258* (2013.01); *A61P 21/00* (2018.01); *A23V 2002/00* (2013.01); *A23V 2200/316* (2013.01); *A23V 2250/2124* (2013.01)

(58) Field of Classification Search
None
See application file for complete search history.

(56) References Cited

FOREIGN PATENT DOCUMENTS

| KR | 10-2015-0095708 | 8/2015 |
| KR | 10-2017-0001037 | 1/2017 |
| KR | 10-2017-0094292 | 8/2017 |

OTHER PUBLICATIONS

Lee et al. (2020) The American J. Chinese Med. vol. 48, No. 3, 631-650. (Year: 2020).*
Bae et al. (2014) Nat. Prod. Chem. Res. 2:5. (Year: 2014).*
Go et al. (2017) J. Ginseng Res. 41: 608-614. (Year: 2017).*
Lobina et al. (2014) Future Oncol. 10(7): 1203-1214. (Year: 2014).*
Ma et al. (2017) Molecules 22: 237 (14 pages) (Year: 2017).*
Park et al. (2020) Molecules 25: 3128 (17 pages) (Year: 2020).*
Raskin et al. (2004) Current Pharmaceutical Design 10, 3419-3429. (Year: 2004).*
Yi et al. (2020) J. Ginseng Res. 44: 58-66. (Year: 2020).*
Fengyu Li et al., "Ginsenoside Rg1 prevents starvation-induced muscle protein degradation via regulation of AKT/mTOR/FoxO signaling in C2C12 myotubes", Experimental and Therapeutic Medicine, vol. 14, pp. 1241-1247, 2017.
Tony Tong-Lin Wu et al., "Induction of apoptosis in prostate cancer by ginsenoside Rh2", Oncotarget, vol. 9, No. 13, pp. 11109-11118, 2018.
Anne Ulrike Trendelenburg et la., "Myostatin reduces Akt/TORC1/p70S6K signaling, inhibiting myoblast differentiation and myotube size", AJP-Cell Physiol, vol. 296, p. C1258-C1270, 2009.
Ashley L Siegel et al., "Muscle satellite cell proliferation and association: new insights from myofiber time-lapse imaging", Skeletal Muscle, vol. 1, No. 7, 2011.
Tomoyoshi Aoyagi et al., "Cancer cachexia, mechanism and treatment", World Journal of Gastrointestinal Oncology, vol. 7, Issue 4, pp. 17-29, Apr. 15, 2015.
Antonella Riva et al., "Protective effect of Panax ginseng in cisplatininduced cachexia in rats", Future Oncology, vol. 10, No. 7, pp. 1203-1214, 2014.
Hyeong-Geug Kim et al., "Antifatigue Effects of Panax ginseng C.A. Meyer: A Randomised, Double-Blind, Placebo-Controlled Trial", PLOS ONE, vol. 8, Issue 4, Apr. 2013.
PE Porporato, "Understanding cachexia as a cancer metabolism syndrome", Oncogenesis, vol. 5, 2016.
Yulia Elkina et al., "The role of myostatin in muscle wasting: an overview", J Cachexia Sarcopenia Muscle, vol. 2, pp. 143-151, 2011.
Michael J. Tisdale, "Reversing cachexia", Cell, vol. 142, Aug. 2010.
LP Christensen, "Ginsenosides chemistry, biosynthesis, analysis, and potential health effects.", Advances in Food and Nutrition Research, vol. 55, 2009, abstract only.
Paolo Bonaldo et al., "Cellular and molecular mechanisms of muscle atrophy", Disease Models & Mechanisms, vol. 6, pp. 25-39, 2013.
MJ Tisdale, "Cancer cachexia", Current Opinion in Gastroenterology, vol. 26, No. 2, pp. 146-151, 2010, abstract only.
Hye-Min Lee et al., "Effect of Ginsenoside Rg3 and Rh2 on Glucose Uptake in Insulin-resistant Muscle Cells", J. Korean Soc. Appl. Biol. Chem., vol. 53, No. 1, pp. 106-109, 2010.

* cited by examiner

*Primary Examiner* — Russell G Fiebig
(74) *Attorney, Agent, or Firm* — Lex IP Meister, PLLC

(57) ABSTRACT

The present invention provides a pharmaceutical composition or food composition for preventing, alleviating or treating muscular diseases comprising ginsenoside Rh2 as an active ingredient.

5 Claims, 5 Drawing Sheets

[FIG. 1]
C2C12 cell line
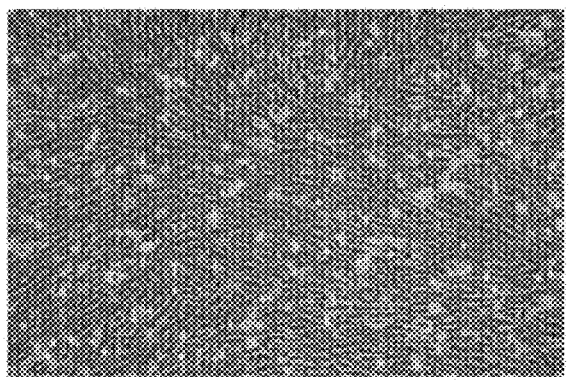 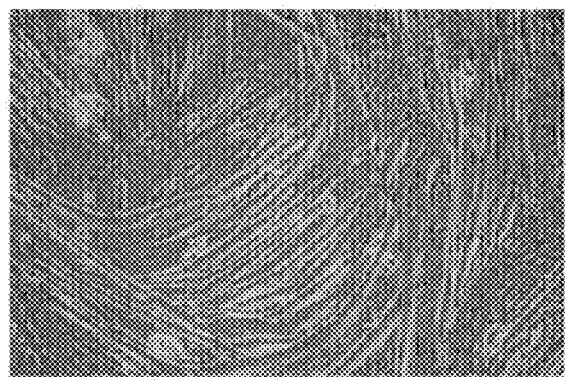
Before differentiation
Before induction of horse serum
After differentiation
After induction of horse serum

[FIG. 2]
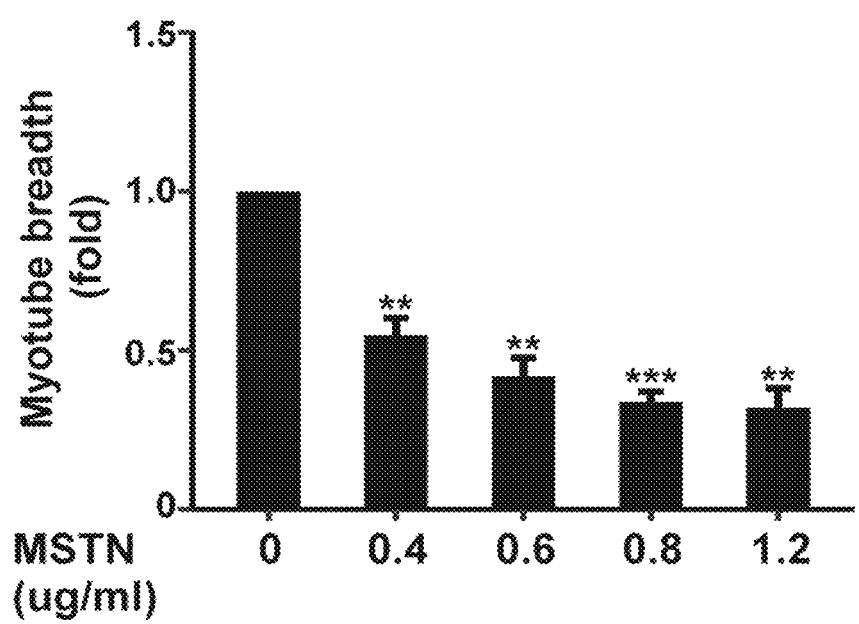

[FIG. 3]
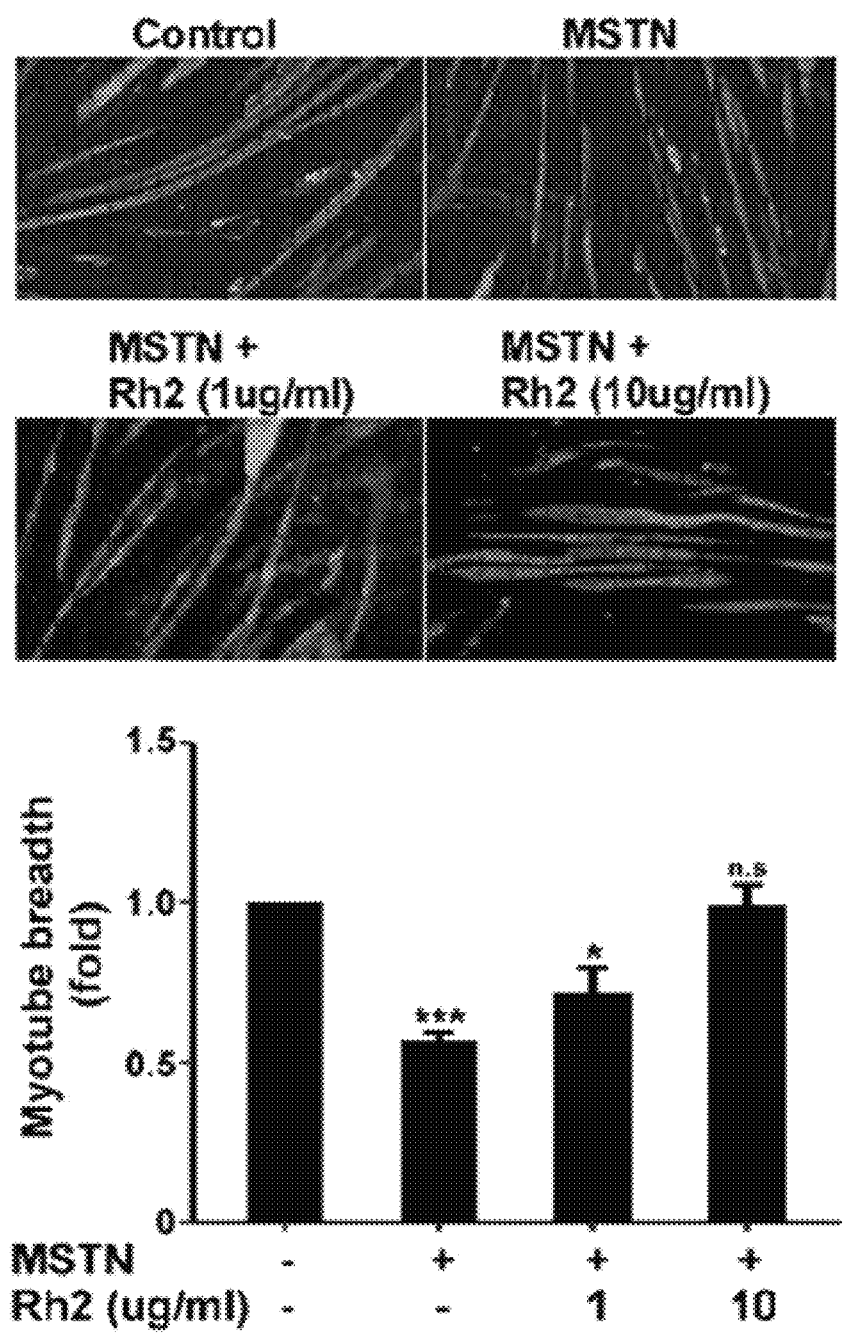

[FIG. 4]
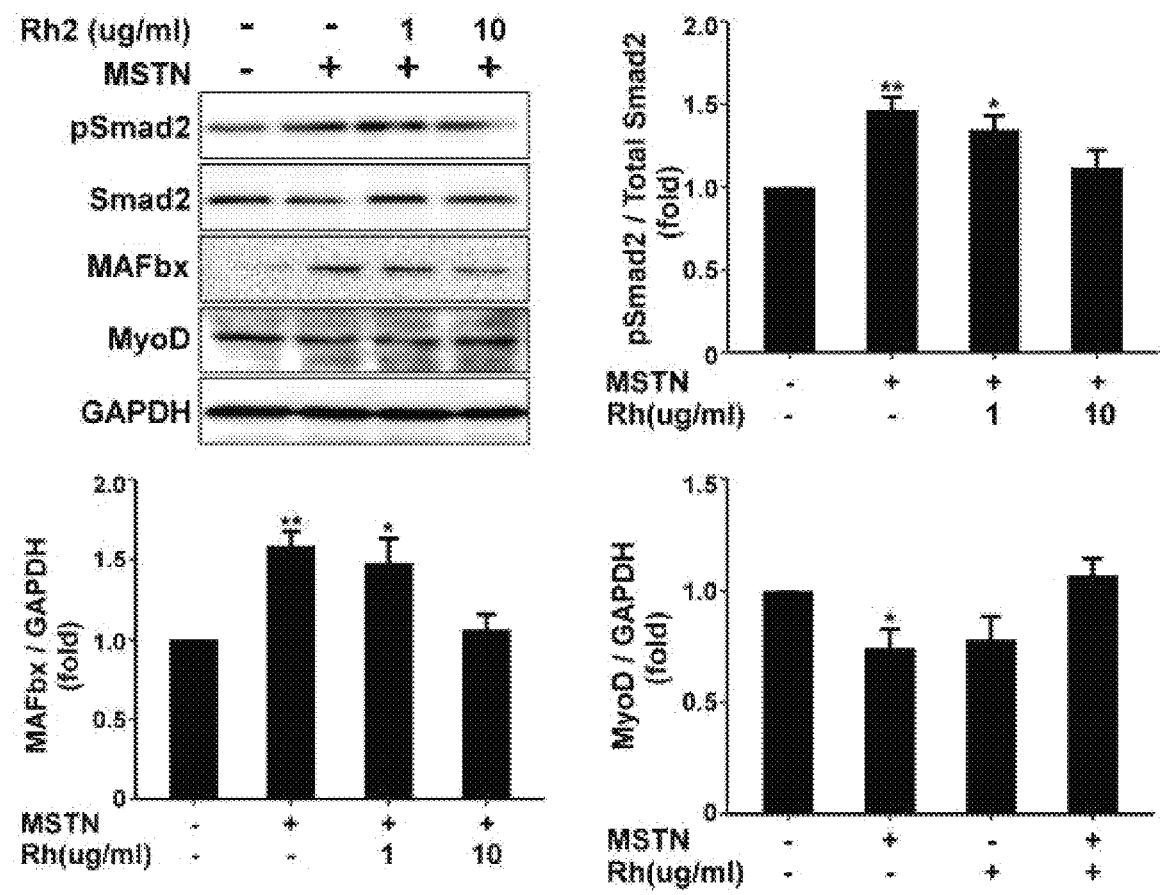

[FIG. 5]
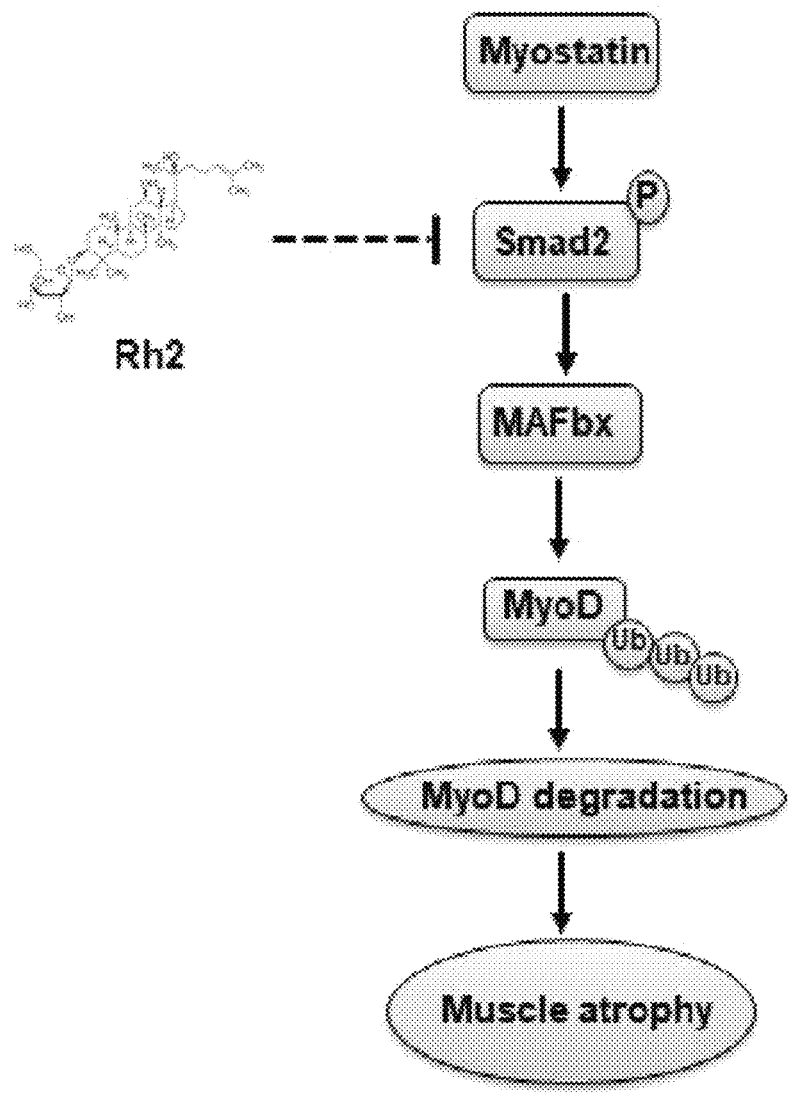

PHARMACEUTICAL COMPOSITION FOR IMPROVING, PREVENTING OR TREATING MUSCLE RELATED DISEASE COMPRISING GINSENOSIDE RH2

TECHNICAL FIELD

The present invention relates to a pharmaceutical composition and a food composition for improving, preventing or treating muscle related diseases for example, muscular atrophy disease, including ginsenoside Rh2.

BACKGROUND ART

Muscles are the largest tissue organ in the human body. The proper amount of muscle mass of the human body is essential for maintaining the structure of the human body, allowing each organ to perform its function, and preventing various diseases.

In order to form muscles, myosatellite cells are first activated and the activated myosatellite cells are differentiated into myoblasts (Siegel L Ashley et al., Skeletal Muscle, 2011, 1, 1-7). Several myoblasts are sorted, fused and differentiated into myocytes through myogenesis. Muscle cells are the fibrous cells having contractility and constituting the muscles. They are also called as myofiber or myotube. These muscle cells are formed and bundled to finally form muscles. The contraction function of muscle is determined by myofibrils in muscle cells. Myofibrils are composed of long proteins such as actin, myosin, and titin and contract by interacting with myofibrils.

Atrophy is degenerative degeneration of muscle tissue caused by various diseases including cancer, diabetes, and the like, and is in loss of mobility caused by the attenuation of morphological function. Thus, the problem of muscular atrophy can be determined by the number and size of muscle cells containing myofibrillar proteins. Unlike sarcopenia caused by aging, the number of myocytes does not decrease in the muscular atrophy caused by disease, but the size of myocytes decreases by the decreased synthesis and the increased degradation of myofibrillar protein (Bonaldo P. et al., Disease Models & Mechanisms, 2013 5:25-39).

Currently, there is no effective way to treat muscular atrophy. The conventional treatments, including megestrol acetate, the drug approved by the FDA, focus on relieving the symptom of atrophy by stimulating appetite (Tomoyoshi Aoyagi et al., World Journal of Gastrointestinal Oncology, 2015, 7 (4): 17-29).

Recently, the signal transduction pathway for explaining the size reduction of muscle cell due to muscular atrophy have been identified. Activin receptor IIB (ActRIIB) is a key receptor of signal transduction of muscular atrophy that has been known to induce atrophy through various mechanisms. The ActRIIB signal increased the expression of MAFbx (muscle-specific ubiquitin-ligase) of an E3 ligase, through the pathway of Smad-MAFbx, Akt-FoxO-MAFbx and MAPK-MAFbx, thereby inducing the ubiquitin proteasome pathway (UPP)-based MyoD protein degradation (Yulia E. et al., Journal of Cachexia, Sarcopenia and Muscle, 2011 September; 2 (3): 143-151). MyoD is a transcription factor that regulates the transcription of various myofibrillar proteins and UPP-based MyoD degradation is known to be a major mechanism of muscular atrophy (Tisdale M J., Current Opinion in Gastroenterology, 2010, 26 (2): 146-151). Myostatin (MSTN, growth differentiation factor 8, GDF-8), on the other hand, is a ligand that binds to and activates ActRIIB, causing the inhibition of myogenesis. ActRIIB activated by MSTN phosphorylates and activates Smad2 and phosphorylated Smad2 (pSmad2) increases the expression of MAFbx (Anne Ulrike Trendelenburg et al., American Journal of Physiology Cell Physiology, 2009, 296 (6) 1270., Lars P. Christensen, Advances in Food and Nutrition Research, 2009, 55, 1-99).

Ginseng and red ginseng contain unique saponins which exist only in ginseng and exhibit their unique pharmacological activity. To date, 150 saponins have been known. Ginseng saponin is classified into protopanaxadiol-based ginsenosides, protopanaxadiol-based ginsenosides, and oleanolic acid-based ginsenosides based on the structure of aglycons. The pharmacological efficacy differs depending on the sugar type, sugar number or the binding position of a glycon. In particular, the compounds in which a sugar such as glucose, rhamnose, arabinose or xylose is bound to protopanaxadiol and protopanaxadiol of dammarane-based triterpenoid show the specific pharmacological activities. Several studies have reported that ginsenoside Rh2, among 150 kinds of ginseng saponins, has an anticancer effect.

DISCLOSURE

Technical Problem

It is an object of the present invention to provide a pharmaceutical composition and a food composition for improving, preventing or treating muscular diseases comprising ginsenoside Rh2 as an active ingredient.

Accordingly, the present inventors constructed the MSTN-induced atrophic myotube cell model, measuring the width of the myotube cell as an indicator of atrophy phenotype, and quantifying the amounts of the muscular atrophy marker proteins (pSmad2, MAFbx, MyoD) after Rh2 treatment, thereby completing the invention for improvement of ginsenoside Rh2 on the muscular atrophy.

The present invention relates to a method of screening a therapeutic agent of muscular diseases such as muscular atrophy, comprising (i) contacting MSTN-induced atrophic myotube cell model with a candidate agent to be tested, and (ii) measuring the width of the myotube cell as an indicator of atrophy phenotype and quantifying the amounts of the muscular atrophy marker proteins (pSmad2, MAFbx, MyoD) to determine the improvement in the muscular atrophy caused by therapeutic agent.

Another embodiment of the invention is to provide a method of preventing or treating a muscular disease, comprising administering ginsenoside Rh2 represented by the following Formula 1 an active ingredient, to a subject in need.

Technical Solution

In order to achieve the object, the present invention provides a pharmaceutical composition for preventing or treating muscular diseases comprising ginsenoside Rh2, more specifically, ginsenoside Rh2 represented by the following Formula 1 as an active ingredient:

[Formula 1]

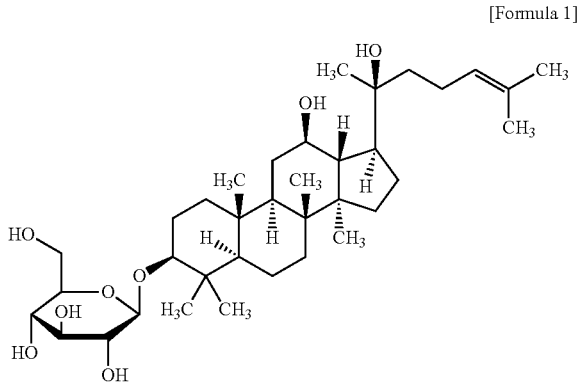

As another embodiment of the present invention, there is provided a food composition for preventing or improving muscular diseases comprising ginsenoside Rh2 as an active ingredient. Another embodiment of the invention is to provide a method of preventing or treating a muscular disease, comprising administering ginsenoside Rh2 represented by the following Formula 1 an active ingredient or a composition comprising the ginsenoside Rh2, to a subject in need. The composition comprising the ginsenoside Rh2 can be an extract of *ginseng* containing ginsenoside Rh2.

As used herein, the phrase "comprising as an active ingredient" means the inclusion of an amount sufficient to achieve efficacy or activity of ginsenoside Rh2. The upper limit of an amount of ginsenoside Rh2 contained in the composition of the present invention can be selected within a suitable range by a person skilled in the art.

The muscular disease may be at least one selected from the group consisting of a muscular atrophy, myopathy, muscular injury, muscular dystrophy, myasthenia, sarcopenia, myocardial infarction, Myoneural conductive disease, dermatomyositis, diabetic amyotrophy, nerve injury, amyotrophic lateral sclerosis (ALS), cachexia, and a degenerative muscular disease, but not limited thereto.

Specifically, the present invention relates to improve the muscular diseases including atrophy by ginsenoside Rh2, which is one of the constituents of *ginseng*, and namely, Rh2 inhibits muscle protein degradation by regulating the mechanism of MSTN-Smad2-MAFbx-MyoD under the condition of suppressing the muscle protein degradation, and increases the width of myotube, thereby improving muscular atrophy.

Hereinafter, the present invention will be described in more detail.

An embodiment of the present invention relates to a pharmaceutical composition for preventing, alleviating or treating muscular diseases comprising ginsenoside Rh2 as an active ingredient.

Specifically, the ginsenoside may have the Formula 1. The ginsenoside Rh2 may be one derived from *ginseng* (*Panax ginseng*), more specifically from red *ginseng* root, *ginseng* root, *ginseng* flower, *ginseng* leaf or *ginseng* fruit.

[Formula 1]

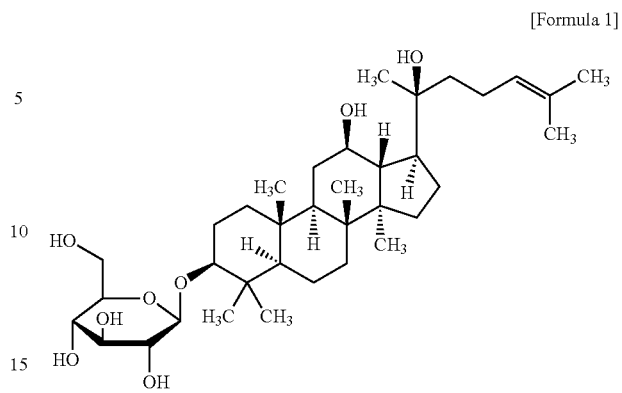

The muscular diseases may be muscular atrophy. More specifically, the present invention relates to a composition for preventing or treating at least one disease selected from the group consisting of muscular atrophy, myopathy, muscular injury, muscular dystrophy, myasthenia, sarcopenia, myoneural conductive disease, in the group consisting of dermatomyositis, diabetic amyotrophy, nerve injury, amyotrophic lateral sclerosis (ALS), cachexia, and degenerative muscular diseases, but not limited thereto.

An embodiment of the present invention is a composition for use in at least one symptom of muscular atrophy symptoms of 1) to 4) or decreased muscular strength caused by muscular atrophy 1) muscular atrophy caused by non-wakefulness, no movement, or weightlessness, 2) muscular atrophy caused by fixation of the extremities or stabilization after surgery, 3) muscular atrophy caused by side effects of steroids, 4) Anorexia in end-stage symptoms of osteoarthritis, chronic joint rheumatism, diabetes, lacerations, infectious diseases with inflammation, sepsis due to infectious diseases, inflammatory bowel disease, collagen diseases, renal failure, liver failure, heart failure, cancer, malignant tumor, cachexia, Or muscular atrophy caused by hyperactivity.

For example, the function of ginsenoside Rh2 improving muscular disease including the muscular atrophy may be applicable to the reduction of muscle size due to diseases such as AIDS, cancer and diabetes, loss of muscle function and improvement of muscular atrophy in a number of muscular atrophy-induced diseases, and can be applied to a functional food composition or a pharmaceutical composition including Rh2 and the like.

The ginsenoside Rh2 may have an effect of improving the width reduction of myotube. The ginsenoside Rh2 functions by inhibiting myostatin-induced atrophy. More specifically, the ginsenoside Rh2 functions by increasing the activity of the transcription factor MyoD through decreasing the phosphorylation of Smad2 and expression amount of MAFbx.

As another embodiment of the present invention, the present invention relates to a composition for preventing, ameliorating, or treating muscular diseases, which comprises the ginsenoside Rh2 as an active ingredient.

The compound of Formula 1 may be isolated from plant extracts or synthesized, or may be used as a commercially available compound. The compound of Formula 1 can be extracted from a plant, for example, *ginseng* by a known extraction method of natural substance. Preferably, the compounds can be extracted by using one or more solvents selected from the group consisting of water, organic solvents having 1 to 6 carbon atoms, and subcritical or supercritical fluids. The organic solvent having 1 to 6 carbon atoms may be an alcohol having 1 to 6 carbon atoms, acetone, ether, benzene, chloroform, ethyl acetate, methylene chloride hexane, cyclohexane, and petroleum ether, but are not limited thereto.

The ginsenoside Rh2 may be derived from red *ginseng* root, *ginseng* root, *ginseng* flower, *ginseng* leaf or *ginseng* fruit. In the present specification, 'muscle' refers to the tendons, muscles, and tendons comprehensively, and 'muscular function' refers to the ability to exert its force by muscle contraction, and muscles exhibit maximum contraction force Muscular endurance which is the ability to indicate how long or how many times the muscle can repeat contraction and relaxation on a given weight, and the ability to exert a strong force in a short period of time. These muscle functions are hosted by the liver and are proportional to muscle mass. The term "muscle function improvement" refers to better improvement of muscle function.

The pharmaceutical composition for prevention and treatment of muscular diseases of the present invention can be used for prevention or treatment of muscular diseases caused by muscle wasting or degeneration.

Muscle exhaustion and degeneration are caused by genetic factors, acquired factors, aging, etc. Muscle exhaustion is characterized by progressive loss of muscle mass, weakening and degeneration of muscles, especially such as skeletal muscle, voluntary muscle and heart muscle. Examples of such diseases are atony, muscular atrophy, muscular dystrophy, muscle degeneration, myotonia, myodystrophy, amyotrophic lateral sclerosis, myasthenia, cachexia, sarcopenia, and the like. The composition of the present invention has an effect of increasing muscle mass, and the kind of muscle is not limited.

The composition for preventing or treating muscular diseases or improving muscle function of the present invention may contain at least one active ingredient which contains the compound of Formula 1 or the *ginseng* extract containing the compound of Formula 1 alone or in combination with other effective ingredient having a similar function thereof. The inclusion of an additional ingredient may further increase the muscle function-improving effect of the composition of the present invention.

The compound of Formula 1 or the *ginseng* extract containing the compound of the present invention has an excellent activity of increasing muscle mass, and thus can be used as an effective ingredient of a pharmaceutical composition.

In addition, the compound of Formula 1 or the *ginseng* extract containing the compound of the present invention can be used as an effective ingredient of a food composition because of its excellent activity for increasing muscle mass.

In addition, the compound of Formula 1 or the *ginseng* extract containing the compound of the present invention has an excellent activity of increasing muscle mass, and thus can be used as an effective ingredient of a pharmaceutic composition.

The pharmaceutical composition according to the present invention can be manufactured in the form of a pharmaceutical composition such as an oral administration agent, a transdermal administration agent, an inhalation administration agent and the like, a food composition such as a functional food, a nut The pharmaceutical composition according to the present invention may further comprise a carrier and a vehicle commonly used in the pharmaceutical field. The pharmaceutical composition may be in the form of granules, powders, coated tablets, tablets, capsules, suppositories, syrups, juices, suspensions, emulsions, drops, injections or sustained release formulations of active compounds. The pharmaceutical composition for prevention and treatment of muscular atrophy can be administered orally or parenterally in various formulations. In the case of formulation, the formulation can be prepared by using a diluent or excipients, such as a filler, an extender, a binder, a wetting agent, a disintegrate, surfactant, and the like On the other hand, the dosage of the pharmaceutical composition according to the present invention may be controlled by considering various factors such as the kind of the disease, the severity of the disease, the kind and amount of the active ingredient and the other ingredients contained in the composition, the type of formulation, age, weight, general health condition or sex of patient, diet, the time of administration, the route of administration and the releasing rate of composition, the duration of the treatment, the drugs administered together, and the like. For example, in the case of an adult, the pharmaceutical composition of the present invention may be administered at a dose of 0.01 to 500 mg/kg once to several times a day. Preferably, 0.1 to 200 mg/kg, more preferably 0.1 to 100 mg/kg, once or three times a day. The unit dosage formulations may be administered several times at predetermined time intervals as necessary.

The pharmaceutical composition of the present invention can be administered to mammals such as rats, mice, livestock, humans, and the like in various routes. All modes of administration may be expected, for example, by oral, rectal or intravenous, intramuscular, subcutaneous, intrauterine dural administration or intracerebral injection.

As another embodiment of the present invention, the present invention relates to a food composition for preventing muscle disorders or improving muscular function comprising the ginsenoside Rh2 as an active ingredient.

The food composition of the present invention can include all functional foods, nutritional supplements, health foods, food additives and feeds, and can be eaten by any animal such as human or livestock. The food compositions of this type may be prepared in various forms according to conventional methods known in the art.

Food compositions of this type may be prepared in various forms according to conventional methods known in the art. General foods include, but are not limited to, beverages (including alcoholic beverages), fruits and processed fruit foods (for examples, canned fruits, bottled fruits, jam, marmalade, etc.), fish, meat and their processed foods (for examples, ham, sausage, corn beef), breads and noodles (for examples, udon, buckwheat noodles, ramen noodles, spaghetti, macaroni, etc.), juice, various drinks, cookies, hard taffy, dairy products (for examples, butter, cheese, etc.), edible vegetable oil, margarine, plant protein, retort food, frozen food, various kinds of seasonings (for examples, soybean paste, soy sauce, sauce, etc.) by adding the compound of Formula 1 or the *ginseng* extract containing the compound of Formula 1. The nutritional supplement, but are not limited to, may be prepared by adding *ginseng* extract or red *ginseng* extract to capsules, tablets, pills, and the like. The health functional food, but not limited thereto, for example, the *ginseng* extract itself may be prepared in the form of tea, juice, and drink, to be liquefied, granulated, or encapsulated. In order to use the *ginseng* extract in the form of a food additive, the *ginseng* extract may be prepared in the form of a powder or a concentrated liquid. In addition, the *ginseng* extract can be prepared in the form of a composition by mixing with an active ingredient known to have properties of prevention of muscular disease and improvement of muscle.

The food composition according to the present invention includes all foods such as beverage, meat, chocolate, food, confectionery, pizza, ramen, other noodles, gums, ice cream, alcoholic beverages, vitamin complexes and the like. The compound of Formula 1 or the *ginseng* extract containing the compound of Formula 1 may be added within a range that does not impair the inherent taste of the food, and is usually in the range of 0.01 to 50% by weight, preferably 0.1 to 20% by weight based on the food. In the case of foods in the form of granules, tablets or capsules, they may be added usually in the range of 0.1 to 100% by weight, or preferably 5 to 100% by weight.

In the present invention, there is no particular limitation on the kind of food, and it includes all foods in a conventional sense. The foods to which the present invention can be applied include, for example, beverages, gums, vitamin complexes, and drinks. When the food composition of the present invention is in the form of a drink, it may contain various flavors or natural carbohydrates as an additional ingredient contained in the general beverages. Examples of the natural carbohydrate include monosaccharides such as glucose, fructose and the like; disaccharides such as maltose, sucrose, and the like; polysaccharides such as conventional sugars such as dextrin and cyclodextrin; and sugar alcohols such as xylitol, sorbitol, erythritol and the like. Besides those described above, the flavoring agents (saccharin, aspartame, etc.) may also be used.

The food composition of the present invention may include nutrients, vitamins, minerals (electrolytes), a flavoring agent such as synthetic flavors and natural flavors, colorants and enhancers (cheese, chocolate etc.), pectic acid and its salts, alginic acid and its salt, organic acids, protective colloid of thickening agents, pH adjusting agents, stabilizers, preservatives, glycerin, alcohols, carbonating agents used in carbonated drinks, and the like.

Advantageous Effects of Invention

The composition of present invention has an effect of improving the decreased width of myotube and increases the activity of the transcription factor MyoD through reduction of the expression amount of MAFbx and phosphorylation of Smad2. Thus, it is possible to provide a composition for preventing, alleviating, and treating muscular diseases including atrophy, which comprises ginsenoside Rh2 as an active ingredient.

BRIEF DESCRIPTION OF DRAWINGS

FIG. 1 is a microscope image showing that C2C12 myoblasts cultured with Horse Serum differentiate into myotube cells.

FIG. 2 is a graph showing the reduced width of differentiated myotube cells shown in FIG. 1 added with various concentrations of MSTN FIG. 3 shows the inhibitory effect of ginsenoside Rh2 on the reduction of myotube cell width in the MSTN-induced atrophic myotube cells. The left side is a photomicrograph showing the width change of myotube cell at the treatment condition of MSTN and Rh2, and the right side is a graph quantifying the width reduction effect according to the concentration of ginsenoside Rh2.

FIG. 4 shows the inhibitory effect of ginsenoside Rh2 on MyoD degradation pathway in the MSTN-induced atrophic myotube cells. The increase and decrease in the expression level of the proteins related to MyoD degradation pathway were quantified by the Western blotting as the increased concentration of ginsenoside Rh2.

FIG. 5 shows the inhibition mechanism of MyoD degradation by ginsenoside Rh2 in MSTN-induced atrophic myotube cells.

MODE FOR INVENTION

Hereinafter, the present invention will be described in detail with reference to Examples. However, the following examples are illustrative of the present invention, and the present invention is not limited by the following examples.

Experimental Example 1: C2C12 Myotube Cells Differentiation and Induction of Muscular Atrophy Cell Model The model of muscular atrophy was constructed by differentiating mouse myoblast cell lines (C2C12 ATCC CRL-1772) into myotube cells followed by treating with MSTN.

Specifically, the cell lines were cultured in DMEM (Gibco) supplemented with 10% (v/v) Fetal Bovine Serum (FBS), 100 U/ml penicillin and 100 U/ml streptomycin (Sigma) at 37° C. in 5% CO2. For differentiating the cell lines into myotube cells, the cells were grown to 80-90% confluence and then cultured in DMEM supplemented with 2% (v/v) horse serum (Horse Serum, HS, Gibco). To verify the differentiation into myotube cells, the merge of multiple myoblasts to one long myotube cells were observed by the microscopic images. FIG. 1 shows microscopic images with differentiation of C2C12 myoblasts to myotube cells by incubation with horse serum.

In order to induce an atrophy model, differentiated myotube cells were cultured in serum-free DMEM medium for 3 hours, and then MSTN was treated with 0.4 μg/ml, 0.6 μl/ml, 0.8 μg/ml and 1.2 μg respectively for 24 hours. MSTN-untreated cells were used as control.

To determine whether the atrophy model was successfully induced, changes in the width of the myotube cells after induction of atrophy were measured. C2C12 myotube cells were fixed with 4% (w/v) paraformaldehyde (Biosesang) for 15 minutes and then treated with 0.2% (v/v) Triton X-100, and blocked with 5% (w/v) BSA for 6 h. The cells were then stained with Myosin Heavy Chain (MHC) antibody (Santa Cruz, sc-20641, 1: 1000) for 12 h at 4° C. and then incubated with Alexa Fluor 488 conjugated secondary antibody at room temperature for 4 h. Images were acquired via HCS equipment (Molecular Devices) and quantified using ImageJ software. The width of myotube cells was quantified by measuring a total of more than 100 myotube cell widths in randomly selected five regions. The width per myotube was determined as the average of three independent measurements.

FIG. 2 is a graph showing relative widths of myotubes depending on treating concentration of MSTN comparing with control group. The width of control group was showed as 1.0. As a result, the width of myotube treated with 0.4 ug/ml of MSTN was greatly decreased (about 45% compared to the normal), and the width of myotube gradually decreased as the concentration of MSTN increased (about 60% to the normal, FIG. 2). Because of the similar tendency of width reduction at concentrations over 0.4 μg/ml of MSTN treatment group, the present inventors decided MSTN concentration for inducing atrophy model in subsequent experiments to 0.4 μg/ml. The results were shown in FIG. 2.

Experimental Example 2: Confirmation of Cell Size Promotion in Atrophic Myotubes by Rh2

To investigate the effect of Rh2 on MSTN-induced atrophy, myotubes were treated with 0.4 ug/ml MSTN alone for 24 hours or treated with combination of 0.4 ug/ml MSTN and 1 ug/ml or 10 ug/ml Rh2 (Sigma, 73658) for 24 hours. In order to measure the change of the myotube width, the myotube cells were stained with MHC antibody as in the above Experimental Example 1, and cell images were obtained using HCS, and the width of myotube was quantified using ImageJ.

The left side of FIG. 3 is showing the stained cell image, and the right side is a graph of the relative value of the control group by quantifying the width of myotube. Experimental results showed that ginsenoside Rh2 inhibits the decrease of width of myotube induced by MSTN and maintains the myotube width above normal level (FIG. 3). The width of myotube treated with MSTN was reduced about 50% compare to normal cells, and when the cells were treated with combination of MSTN and 1 ug/ml Rh2, the width of myotube was about 70% of that of normal cells. When cells were treated with combination of 10 ug/ml Rh2 and MSTN, the width was maintained above 100% of that of normal. These results confirm that Rh2 inhibits MSTN induced atrophy depending on the concentration. The results are shown in FIG. 3.

Experimental Example 3: Confirmation of the Inhibitory Effect of Rh2 on MyoD Degradation Pathway in Atrophic Myotube Cells MSTN is known to induce atrophy by increasing UPP-mediated protein degradation through activation of the ActRIIB-Smad2 signaling pathway. Phosphorylated Smad2 (pSmad2) activates this UPP-mediated proteolytic signaling. Activated UPP is involved in the degradation of MyoD and is regulated by the E3 ligase, MAFbx. To investigate the mechanism of Rh2 in this signal transduction, changes of the amount of Rh2-induced phosphorylation of Smad2 and the amount of MAFbx and MyoD expression were determined. For this purpose, myotube cells were treated with 0.4 μg/ml MSTN alone, or with combination of 0.4 μg/ml MSTN and 1 μg/ml or 10 μg/ml Rh2. Western blotting was performed using pSmad2 antibody, MAFbx antibody, and MyoD antibody respectively.

The bands of Western blot and the relative fold change values of pSmad2/Smad2, MAFbx/GAPDH and MyoD/GAPDH in each treatment conditions were shown in FIG. 4. As shown in FIG. 4, the amount of pSmad2 and MAFbx increased to about 50% compared with normal condition, and the amount of MyoD decreased to about 30% of the normal condition, in the case of MSTN alone treatment. When 10 ug/ml Rh2 was treated with MSTN, the amounts of pSmad2, MAFbx and MyoD were kept at the same level as normal conditions.

These results suggest that Rh2 increases the amount of MyoD and reduces the phosphorylation of Smad2 as well as expression of MAFbx, the MyoD ubiquitinases, and the upregulator of UPP activation respectively. Therefore, the inhibition mechanism of Rh2 on MSTN-ActRIIB pathway can be interpreted as inhibition of MAFbx and MyoD degradation through inhibition of Smad2 phosphorylation. The mechanism of Rh2 to inhibit MyoD degradation in the cell model of atrophy is shown in FIG. 5.

The invention claimed is:

1. A method of treating a muscular disease, comprising administering an effective amount of ginsenoside Rh2 represented by the following Formula 1 an active ingredient, to a subject in need:

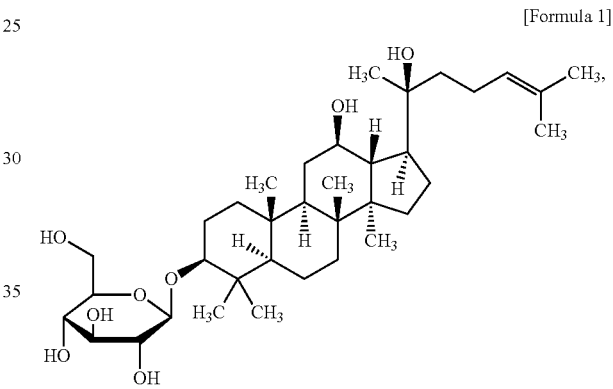

[Formula 1]

wherein the muscular disease is muscular atrophy.

2. The method according to claim 1, wherein the ginsenoside Rh2 is extracted from *ginseng* (*Panax ginseng*).

3. The method according to claim 1, wherein the ginsenoside Rh2 decreases the width of the myotube.

4. The method according to claim 1, wherein the ginsenoside Rh2 inhibits myostatin-induced atrophy.

5. The method according to claim 1, wherein the ginsenoside Rh2 increases the activity of the transcription factor MyoD by reduction of Smad2 phosphorylation, and MAFbx expression level.

* * * * *